(12) United States Patent
Ertas

(10) Patent No.: US 8,360,964 B2
(45) Date of Patent: Jan. 29, 2013

(54) WIDE ANGLE HDTV ENDOSCOPE

(75) Inventor: Hasan Ertas, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1008 days.

(21) Appl. No.: 12/315,686

(22) Filed: Dec. 5, 2008

(65) Prior Publication Data

US 2009/0147076 A1 Jun. 11, 2009

Related U.S. Application Data

(60) Provisional application No. 61/007,002, filed on Dec. 10, 2007.

(51) Int. Cl.
*A61B 1/06* (2006.01)

(52) U.S. Cl. ......... 600/166; 600/111; 600/129; 600/173

(58) Field of Classification Search ............... 348/65, 348/68, 69, 70, 71; 600/101, 109, 167, 168, 600/111, 129, 166, 173, 176
See application file for complete search history.

(56) References Cited

U.S. PATENT DOCUMENTS

| | | | |
|---|---|---|---|
| 3,404,934 A | 10/1968 | Brachvogel et al. | |
| 4,862,873 A * | 9/1989 | Yajima et al. | 600/111 |
| 5,305,736 A * | 4/1994 | Ito | 600/109 |
| 5,459,605 A | 10/1995 | Kempf | 359/462 |
| 5,522,789 A * | 6/1996 | Takahashi | 600/166 |
| 5,584,793 A * | 12/1996 | Sauer et al. | 600/121 |
| 5,598,205 A * | 1/1997 | Nishioka | 348/65 |
| 5,603,687 A * | 2/1997 | Hori et al. | 600/166 |
| 5,630,788 A * | 5/1997 | Forkner et al. | 600/182 |
| 5,743,847 A * | 4/1998 | Nakamura et al. | 600/166 |
| 6,261,226 B1 * | 7/2001 | McKenna et al. | 600/109 |
| 6,471,642 B1 * | 10/2002 | Igarashi | 600/166 |
| 6,498,884 B1 * | 12/2002 | Colvin et al. | 385/117 |
| 6,537,209 B1 | 3/2003 | Pinkhasik et al. | |
| 6,614,595 B2 * | 9/2003 | Igarashi | 359/464 |
| 6,720,988 B1 * | 4/2004 | Gere et al. | 348/45 |
| 6,949,069 B2 | 9/2005 | Farkas et al. | |
| 6,994,668 B2 | 2/2006 | Miyano | |
| 6,997,871 B2 | 2/2006 | Sonnenschein et al. | |
| 7,160,247 B2 | 1/2007 | Deppmeier et al. | |
| 7,170,677 B1 * | 1/2007 | Bendall et al. | 359/464 |
| 7,300,397 B2 * | 11/2007 | Adler et al. | 600/110 |
| 7,544,163 B2 * | 6/2009 | MacKinnon et al. | 600/178 |
| 7,869,140 B2 * | 1/2011 | Duckett, III | 359/753 |
| 8,038,602 B2 * | 10/2011 | Gill et al. | 600/121 |
| 8,075,478 B2 * | 12/2011 | Campos | 600/139 |
| 2004/0015049 A1 | 1/2004 | Zaar | |
| 2004/0125469 A1 * | 7/2004 | Miyano | 359/783 |
| 2004/0249247 A1 | 12/2004 | Iddan | |
| 2004/0254424 A1 | 12/2004 | Simkulet et al. | |
| 2005/0259487 A1 * | 11/2005 | Glukhovsky et al. | 365/202 |

(Continued)

*Primary Examiner* — Lashonda Jacobs
(74) *Attorney, Agent, or Firm* — Flynn, Thiel, Boutell & Tanis, P.C.

(57) ABSTRACT

A wide angle HDTV endoscope includes at least two optical imaging channels. Lenses close each channel at the distal end of the endoscope. The imaging channels each have a different field of view in complementary directions, and have overlapping or cross-over field of view areas. Received images are transmitted along the longitudinal axis of the imaging channels of the endoscope to a camera head that contains a wide screen image sensing device. An external light source provides the required lighting and an image processing device can provide necessary software algorithms to format the images and to control any overlapping or cross-over field of view areas to obtain a single display image. In another arrangement, optical blocking elements provided at the proximal end of the endoscope or within the imaging channels eliminate portions of one or more images from the imaging channels so that at the cross-over areas only a single image is provided to the imaging device.

22 Claims, 14 Drawing Sheets

U.S. PATENT DOCUMENTS

| | | |
|---|---|---|
| 2006/0235273 A1* | 10/2006 | Moriyama et al. ............ 600/113 |
| 2006/0235276 A1 | 10/2006 | Takase et al. |
| 2007/0038031 A1* | 2/2007 | Miyagi et al. ................. 600/182 |
| 2007/0049795 A1* | 3/2007 | Miyagi et al. ................. 600/109 |
| 2007/0049803 A1* | 3/2007 | Moriyama ................... 600/176 |
| 2007/0132839 A1* | 6/2007 | Pang et al. ...................... 348/65 |
| 2008/0091064 A1* | 4/2008 | Laser ............................ 600/109 |
| 2008/0167528 A1* | 7/2008 | Segawa et al. ................ 600/160 |
| 2008/0214895 A1* | 9/2008 | Campos ........................ 600/129 |
| 2009/0030317 A1* | 1/2009 | Levy ............................. 600/447 |

\* cited by examiner

WIDE ANGLE HDTV ENDOSCOPE

CROSS-REFERENCE TO RELATED APPLICATION

This application claims the benefit of U.S. Provisional Application Ser. No. 61/007,002, filed Dec. 10, 2007, which is incorporated herein by reference in its entirety.

FIELD OF THE INVENTION

This invention relates to the endoscopy field, and primarily endoscopes used in minimally invasive surgeries. This invention allows a true wide screen endoscopic image to be created that is sent to a display screen to provide a 16:9 aspect ratio HDTV image with a wide angle view that shows more of an observed surface of an anatomical structure to viewers.

BACKGROUND OF THE INVENTION

In today's minimally invasive surgeries, imaging devices are used to help a surgeon visualize the interior of a patient's body. Depending on the type of procedure, an endoscope is typically inserted into the patient's abdominal area, knee joint, shoulder joint or some other part of the body that requires surgical treatment. As shown in prior art FIG. 1, the endoscope 12 is usually connected at its proximal end to a camera 14 which is connected to an image processing device 16 either via a connecting cable 18 or wirelessly through a radio frequency transmitter and receiver (not shown). The camera 14 usually contains image sensors, such as CCD, CMOS or other kinds of imaging devices. As shown in FIG. 1, an external light source 20 is also usually connected to the endoscope 12 by a fiber optic cable 22. The processing device 16 and light source 20 are shown on shelf unit 23.

As shown in FIG. 2, the endoscopes 12 used in today's minimally invasive surgeries have a circular outer shield 24 and a circular optical system 26 inside the outer shield 24 to transmit an image from a distal end 28 to a proximal end 30. The outer shield 24 is typically stainless steel or a flexible plastic material. The circular optical system 26 generally is either a series of rigid rod lenses or a flexible optical fiber inserted along the longitudinal axis of the endoscope 12. These endoscopes have not changed much over the last decade or so in terms of the way they pick up and transmit an image of a target object from the distal end 28 of the endoscope 12 through the optical system 26 and an optics coupler 34 to image sensors 36 of the camera 14 at the proximal end 30 of the endoscope 12. The circular optical system 26 views objects in the field of view 38 as shown in FIG. 2. An image enters the distal end 38 of the endoscope 12 and travels through circular optical system 26 and optics coupler 34 to the image sensor 36 at the proximal end 30 of the endoscope. Fiber optic cable 22 provides light from light source 20 to a light transmitting optic fiber 40 that outputs illuminating light at the distal end 28 of the endoscope 12. While a single optic fiber 40 is shown, a plurality of optic fibers may output light at the distal end 28 of the endoscope 12.

Prior art endoscopes are initially designed to be used with imaging elements of standard definition (SD) aspect ratio. Such an aspect ratio is also known as 4:3 or 5:4, which is the fraction of the horizontal width of a video image to the vertical height of the image on a display device. Imaging technology and consumer demand, however, have significantly changed recently and the aspect ratio requirement for such endoscope video systems has shifted from the standard definition (SD) aspect ratio to wide screen (also known as high definition (HD) aspect ratio which is typically a width to height ratio of 16:9.

In addition to a wider aspect ratio, advancements in imaging technology have led to higher native acquisition resolutions in both interlaced and progressive scanning modes. Interlaced or progressive scanning usually refers to the way an image is acquired by the image sensor. If the horizontal lines of image are scanned one after another consecutively, then the system is called a progressive scan system. If the horizontal lines of image are scanned by skipping every other line in the first scan followed by a second scan to scan the skipped lines, then the system is called an interlaced scanning system. Whether an interlaced or a progressive scan, the HD resolution includes at least one of the following three well known standards: 1280×720p, 1920×1080i, and 1920×1080p, where i stands for interlaced and p stands for progressive. Although these three formats may have different horizontal and vertical lines of resolution, they all maintain a 16:9 horizontal to vertical aspect ratio. Also known as HDTV standards, these three standards are perceived to show more picture and better picture quality on a display screen. Typically, however, progressive scan systems provide a superior image quality compared to interlaced scan systems. Movies and sports events primarily benefit from these HDTV standards, especially the progressive scan ones, which give a unique viewing angle and feel to their viewers.

Since the imaging and display technologies have advanced from standard definition (SD) resolutions (with 4:3 or 5:4 aspect ratio) to high definition (HD) resolutions (with 16:9 aspect ratio), almost all consumer-grade imaging equipment has shifted over to using a 16:9 aspect ratio. The same technological change has also been affecting the medical markets including endoscopic imaging equipment. The image sensor devices (primarily CCD and CMOS sensors or devices performing a similar function) and the displays (LCDs and plasma screens) have slowly shifted toward a 16:9 aspect ratio in endoscopic imaging applications.

Existing scopes, as used with the existing 4:3 aspect ratio imaging sensors as described above, cause significant loss of viewing area as shown in FIG. 3. The magnified scope image 42 shown in FIG. 3 covers and extends beyond the usable surface area of the generally rectangular imaging device 44 due to the simple geometrical mismatch of the endoscope's circular optical element with a rectangular 4:3 aspect ratio imaging element. Thus, this arrangement shows a problem that already existed with 4:3 aspect ratio imaging elements 44. The mismatch, however, becomes much more unacceptable and undesirable with the use of a HD imaging device 46 having a 16:9 aspect ratio as shown in FIG. 4. Although a 16:9 rectangular imaging device 46 can cover more of the scope's circular image 42 from side to side as compared to a 4:3 imaging device, the 16:9 imaging device 46 receives much less of the scope's circular image 42 vertically upwardly and downwardly compared to the 4:3 imaging device 44 as shown by comparison of FIG. 4 with FIG. 3. In other words, an imaging device 46 having a 16:9 aspect ratio does not maximize the amount of a circular image 42 that can be viewed from an endoscope imaging arrangement. Instead, less of the vertical portions of the image 42 are viewable. This invention offers a solution to minimize or eliminate the problem.

One device that addresses the problem is disclosed in U.S. Pat. No. 6,498,884 to Colvin, et al., whose disclosure is incorporated herein by reference. In the '884 system, multiple rectangular optical channels (lens elements) are used to create an overall rectangular lens system. This arrangement also requires all sides of the individual rectangular lenses to be coated or blackened to minimize glare and refractive errors. Besides the excessively high cost of manufacturing rectangular lenses, such designs usually continue to have optical image quality problems due to the natural corners of the rectangular lens elements no matter what kind of coating is provided for the rectangular lenses. In fact, perfectly coating such lens corners in practical systems is almost impossible. The invention described herein does not require any of the above special requirements and uses readily available rounded optical rod elements and optical fibers or the like.

Another wide viewing endoscope is taught in U.S. Patent Publication 2006/0235276 A1. The '276 publication discloses an endoscope having a plurality of illumination lenses and one objective viewing lens having a wide angle.

SUMMARY OF THE INVENTION

The invention relates to a wide viewing angle endoscope having at least two rounded optical imaging channels for sensing images and providing the images to an image sensor. The invention fits the images from the imaging channels to a rectangular image sensor to increase the field of view of the endoscope.

Figure 1:
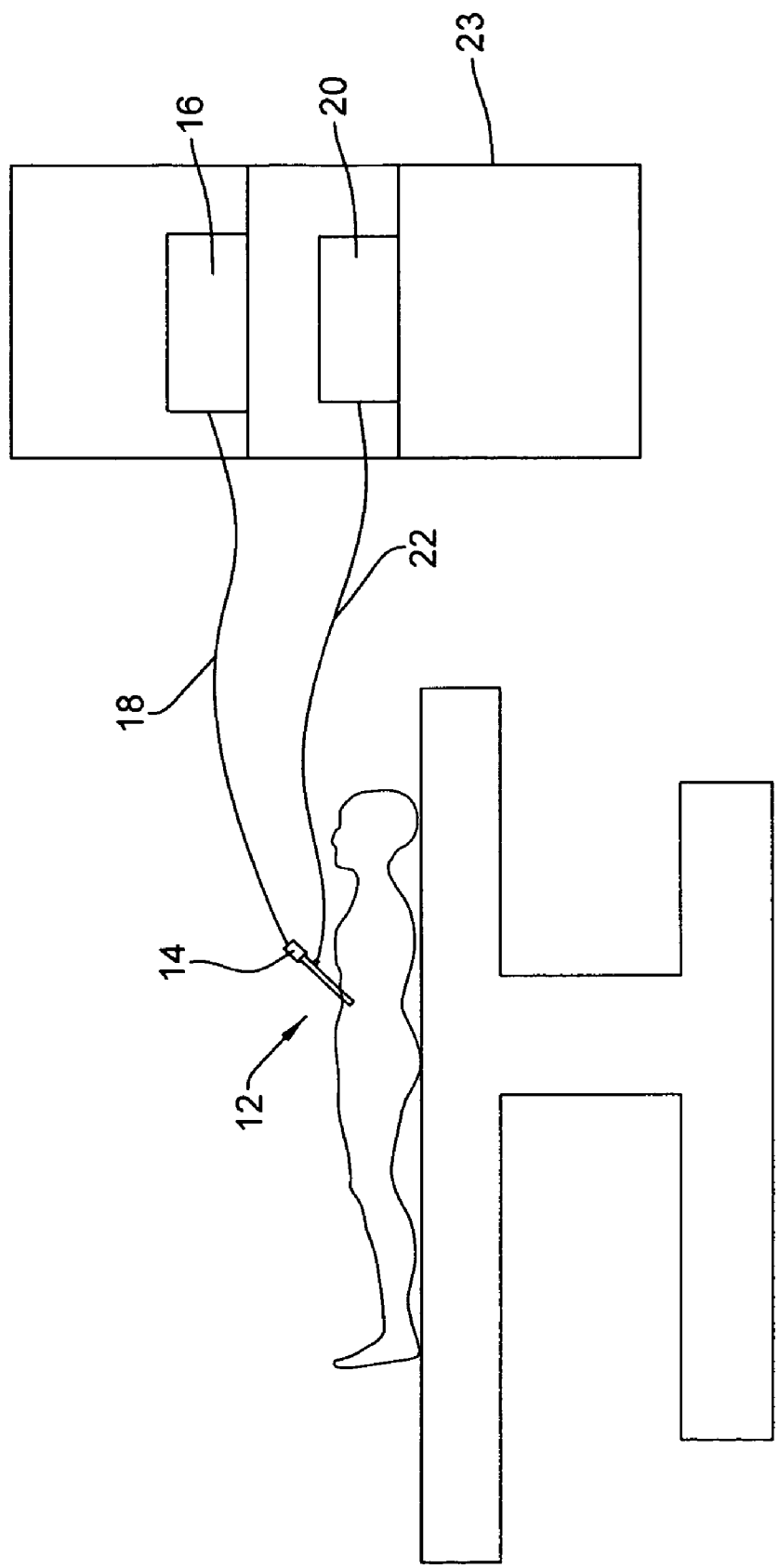
FIG. 1 shows a perspective view of a prior art endoscope system utilized in an operating-room setting.
Figure 2:
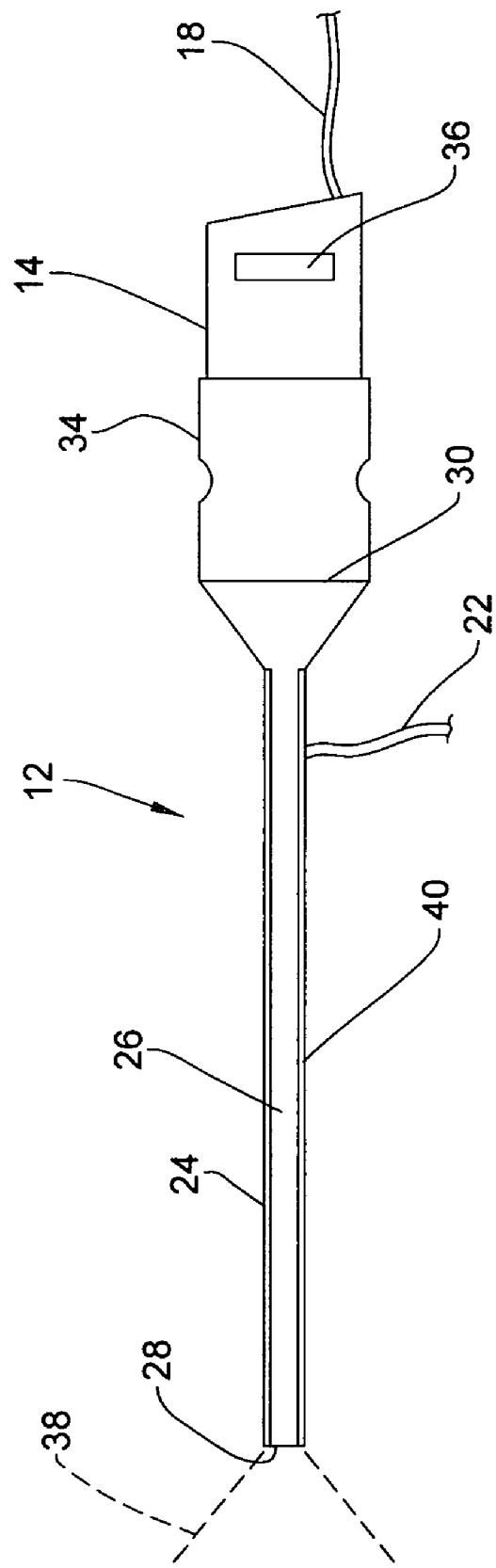
FIG. 2 shows the prior art endoscope illustrated in FIG. 1.
Figure 3:
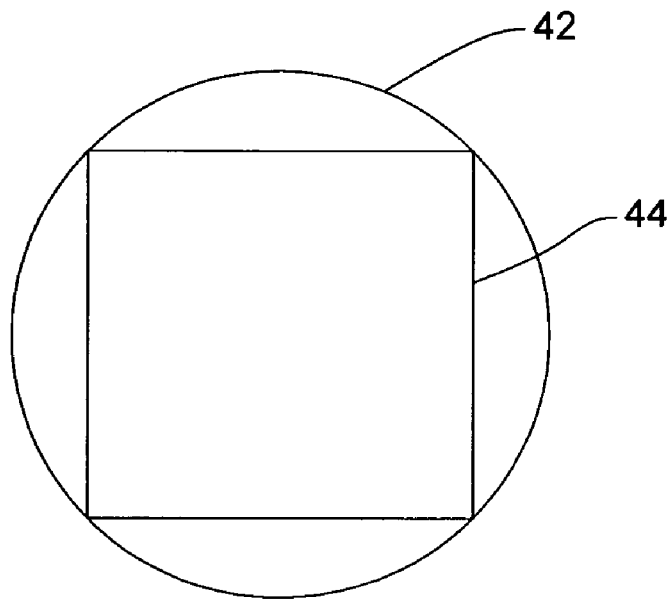
FIG. 3 shows an image from an endoscope projected on a rectangular image sensor having a 4:3 aspect ratio.
Figure 4:
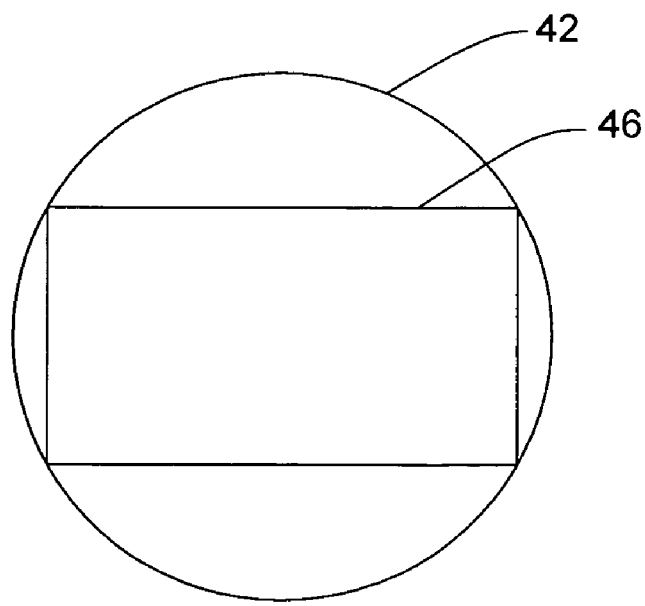
FIG. 4 shows an image from an endoscope projected on a rectangular high definition imaging sensor having a 16:9 aspect ratio.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the tool arrangement and designated parts thereof. The words "forwardly" and "distally" will refer to the direction toward the end of the tool arrangement which is closest to the patient, and the words "rearwardly" and "proximally" will refer to the direction away from the end of the tool arrangement which is furthest from the patient. Said terminology will include the words specifically mentioned, derivatives thereof, and words of similar import.

DETAILED DESCRIPTION

FIGS. 5-9 illustrate one embodiment of the invention. In this embodiment, the distal tip end 48 of the endoscope 50 has a flat circular tip and is rounded or tapered in a longitudinal direction to join with a cylindrical portion of the endoscope 50. As in the prior art, the endoscopic system includes a fiber optic cable 22 connected to external light source 20. A lens coupler 51 is provided at the proximal end of the endoscope 50. Further, the system includes a camera 14 having an image sensor 46 connected by a cable 18 to an image processing device 49.

Figure 6:
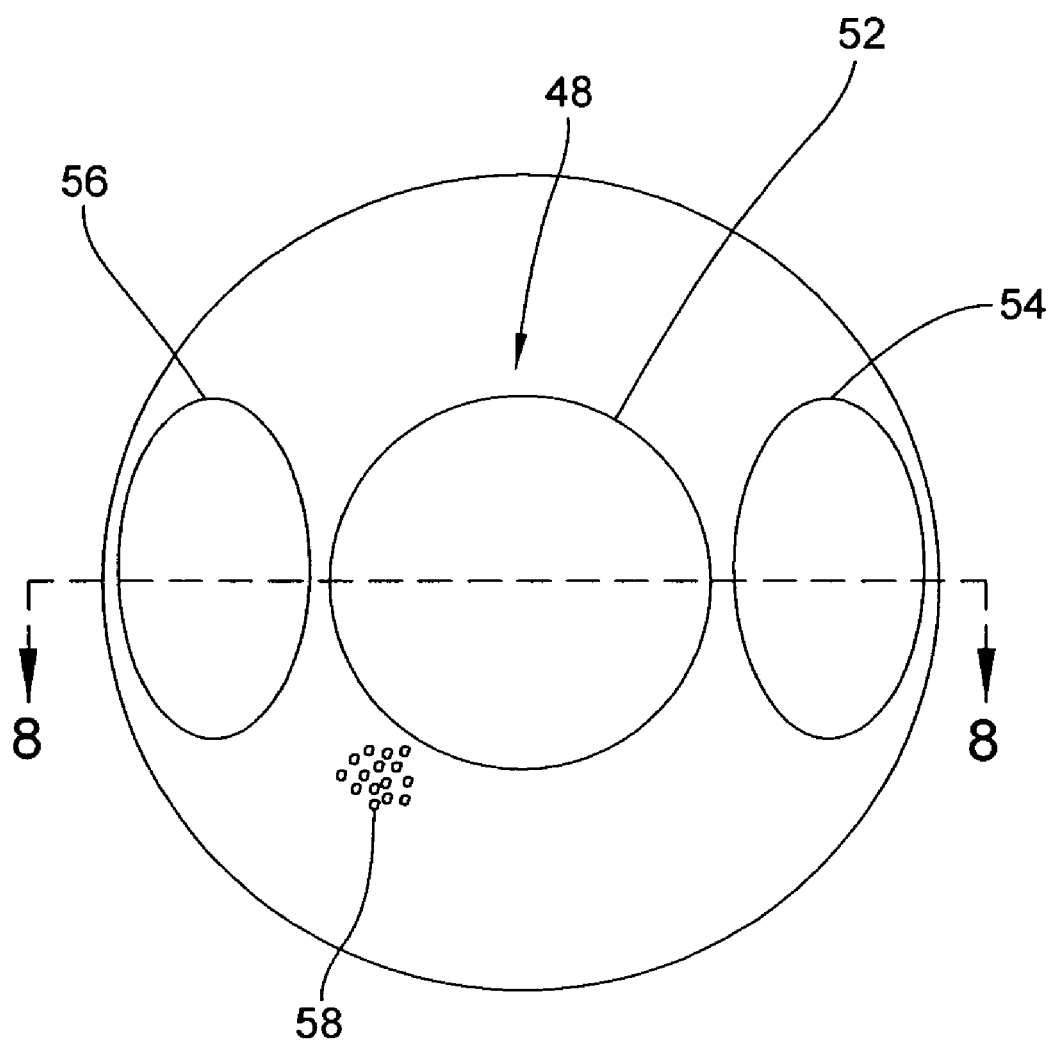
FIG. 6 shows an enlarged front end view of the distal tip end of the endoscope of FIG. 5.
Figure 7:
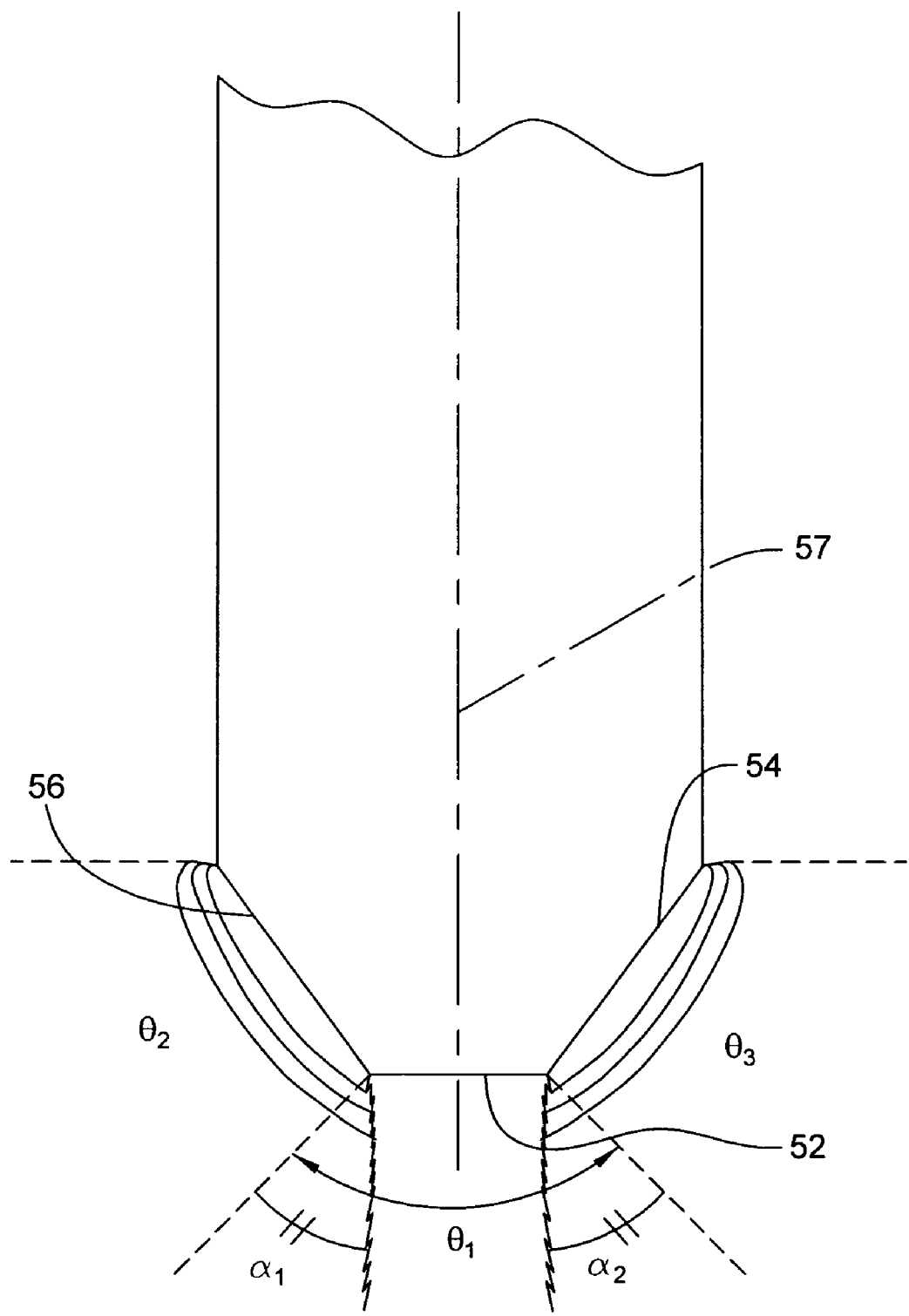
FIG. 7 shows an enlarged top view of the distal tip end of the endoscope of FIG. 5.

A front view of the distal tip end 48 of the imaging endoscope 50 is shown in FIG. 6. The tip end 48 includes a first frontwardly directed central lens 52 and second and third sidewardly oriented lenses 54, 56 symmetrically provided on opposing sides of the center lens 52. While lenses 54, 56 appear elliptical in FIG. 6, the lenses 54, 56 are actually circular in shape, as is central lens 52. In FIG. 7, the lenses 54, 56 are oriented at an outward angle as compared to the central lens 52. The lenses are oriented and shaped so that central lens 52 has a central field of view θ1 projecting longitudinally outwardly from the distal tip end 48 of the endoscope 50. Lens 56 has a field of view θ2 as shown in FIG. 7, and lens 54 has a field of view defined by θ3 in FIG. 7. The fields of view θ2, θ3 have the same size and are symmetric with respect to a longitudinal axis 57 of the endoscope 50.

FIG. 7 also shows an overlap or cross-over in the fields of view θ2, θ3 of the side lenses 54, 56 with respect to the field of view θ1 of the central lens 52. In FIG. 7 the overlap of the field of view of lenses 52, 56 is defined by angle α1 and the cross-over or overlap for the lenses 52, 54 is defined by the angle α2.

The lenses 52, 54, 56, preferably are concave to obtain the desired field of view.

Returning to FIG. 6, in one embodiment the surface at the distal tip end 48 of the endoscope 50, not including the lenses 52, 54, 56, includes a plurality of fiber optics (only some of which are shown) represented by numeral 58 projecting light outwardly from the distal end of the endoscope. The fiber optics 58 are connected to the light source 20. Light projecting outwardly from the fiber optics 58 provides illumination so that the lenses 52, 54, 56 may view an anatomical structure in the interior of a patient's body.

Figure 5:
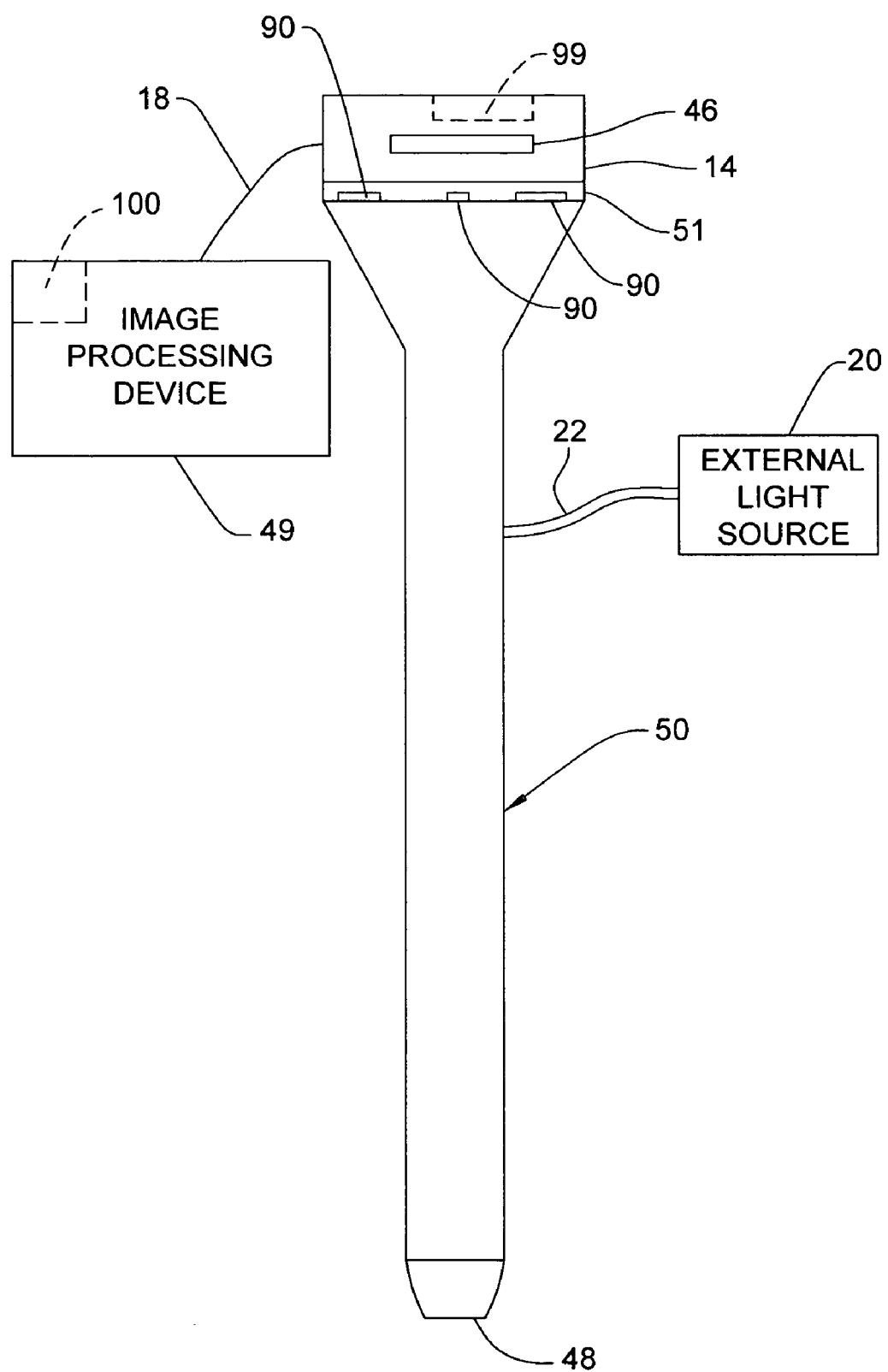
FIG. 5 shows a longitudinal side view of an endoscope system according to the invention.
Figure 8:
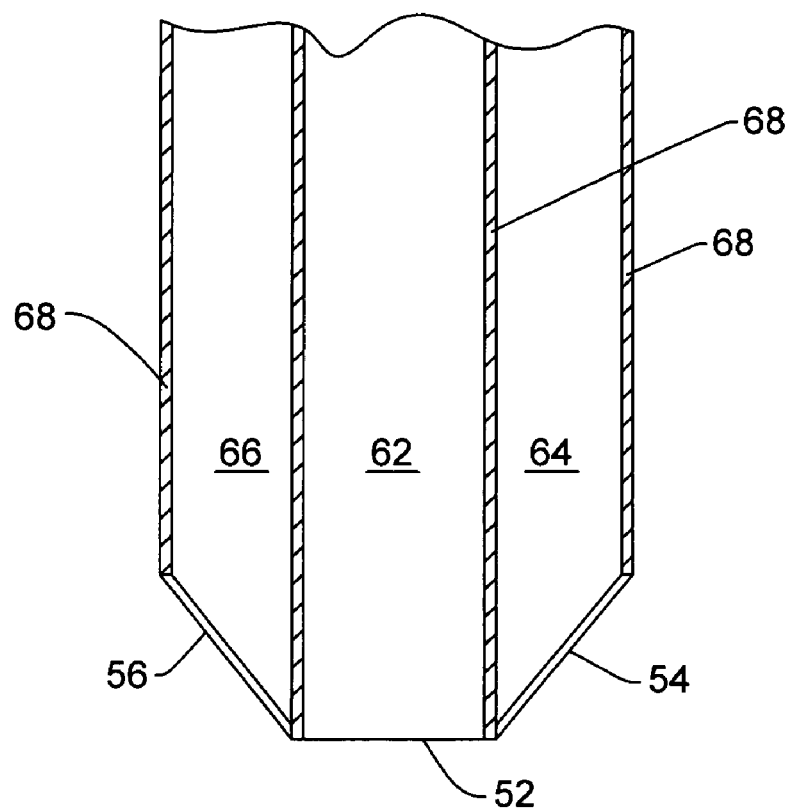
FIG. 8 shows a cross-sectional view of the tip end of the endoscope taken at 8-8 in FIG. 6.

The cross-sectional view of FIG. 8 shows corresponding image channels 62, 64, 66 within the endoscope for each of the image receiving lenses 52, 54, 56. The imaging channels 62, 64, 66 in the illustrated embodiment have a circular cylindrical shape along the longitudinal lengths thereof and are defined by cylindrical walls 68. The imaging channels 62, 64, 66 extend the length of the endoscope 50 and open at the proximal end 70 of the endoscope. Openings 72, 74, 76 shown at the proximal end 70 in FIG. 9 correspond to the imaging channels 62, 64, 66, respectively. As shown in FIG. 5, in one embodiment the imaging channels 62, 64, 66 join with optical coupler 51 to provide images to the imaging device 46.

Operation

Figure 11:
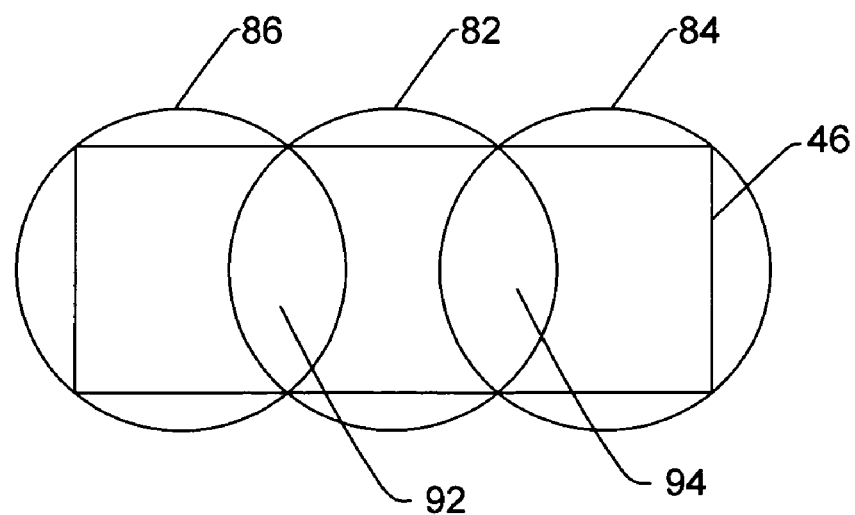
FIG. 11 shows the images from the proximal end of the endoscope projected onto an image sensor.
Figure 9:
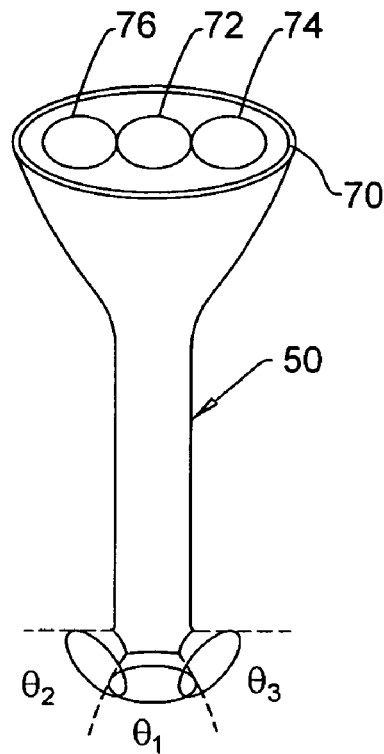
FIG. 9 shows a perspective view of the endoscope of FIG. 5.

Light source 20 provides light that passes through fiber optics 58 and outwardly from the distal tip end 48 of the endoscope 50 to illuminate an anatomical structure in a patient's body. Reflected light images pass through the lenses 52, 54, 56 at the distal tip end 48 of the endoscope 50 and into the imaging channels 62, 64, 66 shown in FIG. 8. The images pass through the imaging channels 62, 64, 66 and are refocused by lens coupler 51 (not shown in FIG. 10) to form corresponding images 82, 84, 86. Image 82 is the central image. FIG. 11 shows how the images 82, 84, 86 coact with a 16:9 aspect ratio imaging device 46 of a camera 14. The image sensor 46 converts the images to electrical signals. The electrical signals are provided to the image processing device 49.

In FIG. 11, the projected images 82, 84, 86 completely cover the entirety of the image sensor 46, but also contain overlapping regions 92, 94 wherein the side images 84, 86 from the side imaging channels 64, 66 share a portion of the field of view of the central image 82.

In a first embodiment of the invention, the overlap or crossover of the images in regions 92, 94 is prevented by optical blocking elements 90 in the lens coupler 51 as shown in FIG. 5. The optical blocking elements 90 can comprise secondary optics, mechanical stoppers, mechanical blockers, or optical image stoppers located at the proximal end 70 of the endoscope 50 for eliminating the image from one or more of the imaging channels 62, 64, 66 only in the cross-over areas 92, 94 so that only one image is provided thereat. In some embodiments, the stoppers are formed by light absorbing coatings. The image sensed by imaging device 46 is then sent to the image processing device 49 and forwarded to a video display.

While the blocking elements 90 are a part of the lens coupler 51 at the proximal end 70 of the endoscope 50 in FIG. 5, in some embodiments the blocking elements are located within one or more of the channels 62, 64, 66 to provide the blocking effect.

In another embodiment of the invention, the image processing device 49 connected to the camera 14 processes the scanned images 82, 84, 86 captured by the image sensor 46 and utilizes image correction algorithms or software filters to eliminate the effect of the multiple images applied in the cross-over areas 92, 94 to provide an accurate image for display in the cross-over areas. In yet another embodiment, the algorithms or software filters are provided by a separate processor device located within the camera 14.

The above embodiments prevent blurry outcomes when two images are mapped over one another in the cross-over areas 92, 94. The blurriness is due to the adjacent channels 62, 64, 66 viewing the same point of an object from a different angle at the distal tip end 48 of the endoscope 50.

While the lenses 52, 54, 56 illustrated in FIG. 6 are all circular relative to the surrounding surface of the distal tip end 48, in some embodiments the lenses 52, 54, 56 and the imaging channels 62, 64, 66 have an elliptical shape. An important factor is that the image sensor 46 is completely enclosed by the images 82, 84, 86 received through the lenses 52, 54, 56 and the imaging channels 62, 64, 66. While the image sensor 46 is illustrated as a single rectangular element in FIGS. 5 and 11, plural elements, such as three elements defining a rectangular shape are also contemplated.

Figure 12:
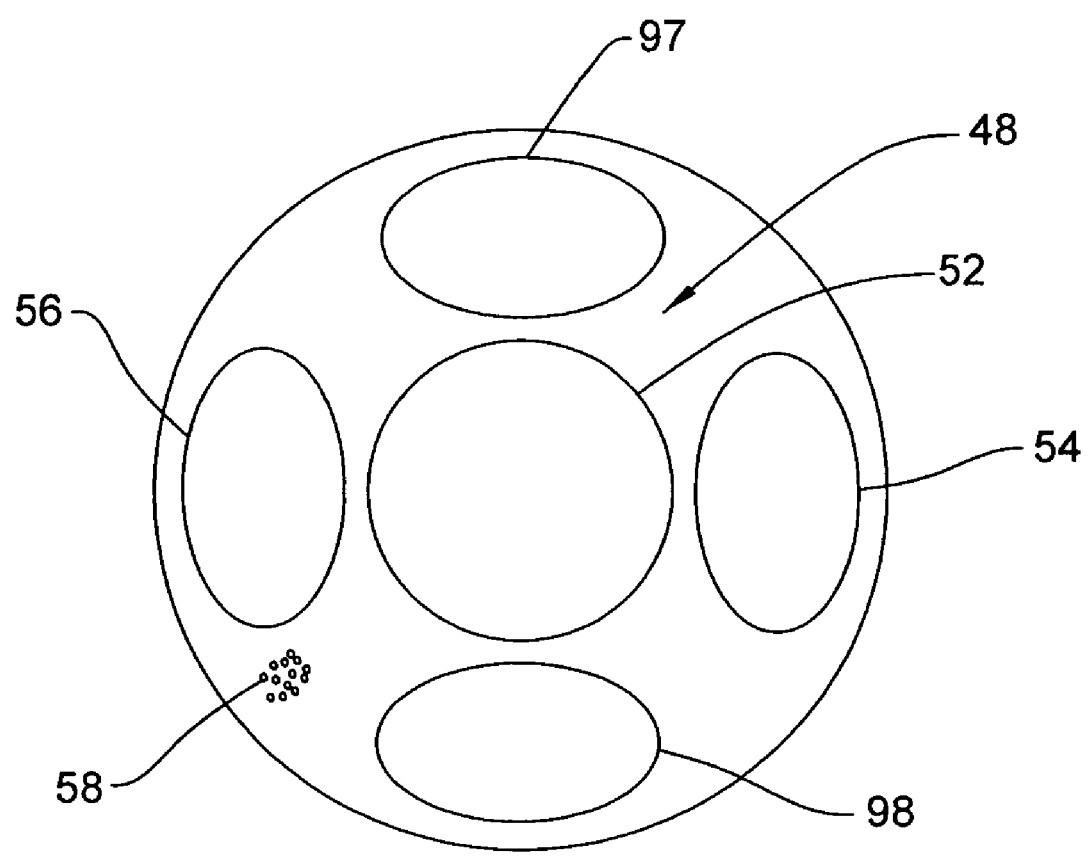
FIG. 12 shows a front view of the distal end tip of another embodiment of the endoscope.

FIG. 12 shows another embodiment of the endoscope 50. FIG. 12 corresponds to the distal tip end 48 illustrated in FIG. 6 having lenses 52, 54, 56. Also included at the distal tip end 48, however, are additional lenses 97, 98 and corresponding image channels. Thus each lens 52, 54, 56, 97, 98 each have their own image channel.

The endoscope of FIG. 12 is rotatable relative to the imaging device 46 of the camera 14. When rotated 90°, the central lens 52 transfers an image through the imaging channel 62. This results from the additional lenses 97, 98 transferring images through respective imaging channels similar to the images transferred through lenses 54, 56 to create the images 82, 84, 86 at the proximal end of the endoscope 50 as shown in FIG. 11. Thus, a cross-sectional view of the distal end taken in a perpendicular plane across the channels of lenses 52, 97, and 98 would appear substantially the same as the cross-sectional view of FIG. 8.

Figure 13:
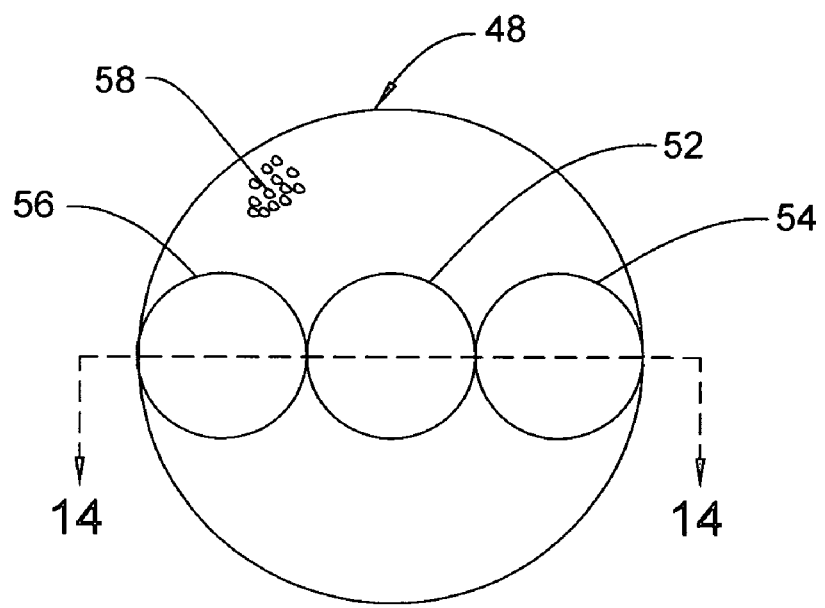
FIG. 13 shows an enlarged front end view of another embodiment of the endoscope.
Figure 14:
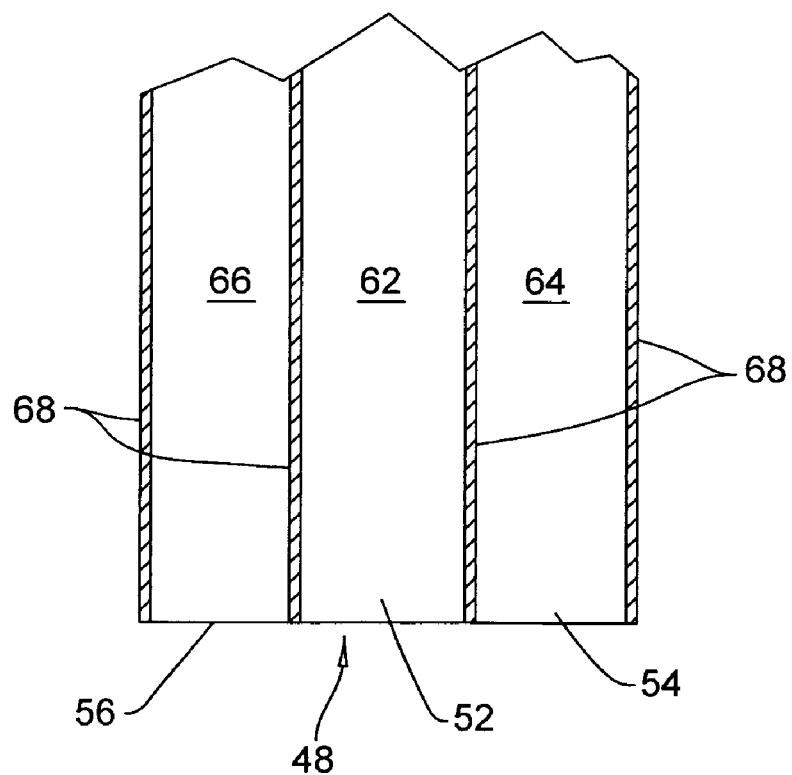
FIG. 14 shows a cross-sectional view of the tip end of the endoscope taken at 14-14 of FIG. 13.

FIGS. 13 and 14 show another embodiment of the endoscope 50. In this embodiment the circular lenses 52, 54, 56 are provided at a flat distal tip end 48 of the endoscope 50. Thus the tip end 48 has a cylindrical shape. The lenses 52, 54, 56 have fields of view that provide overlapping images that can be similar to the fields of view shown in the earlier embodiment illustrated in FIGS. 7 and 9. Further, in some embodiments the fields of view need not extend sidewardly and outwardly to the extent of the fields of view θ2 and θ3 in FIG. 7.

Figure 15:
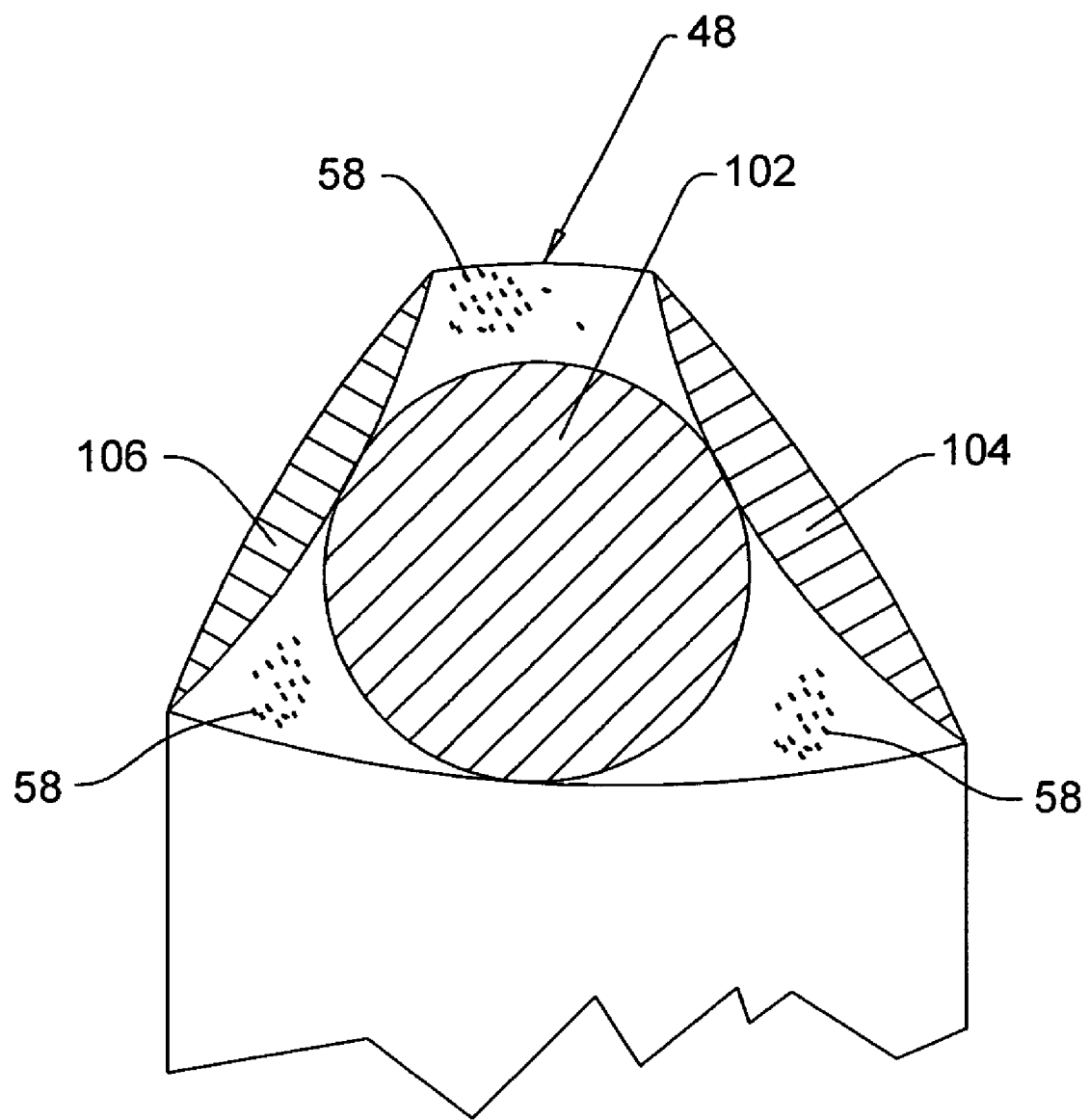
FIG. 15 shows an enlarged top end view of the distal tip end of another embodiment of the endoscope.
Figure 16:
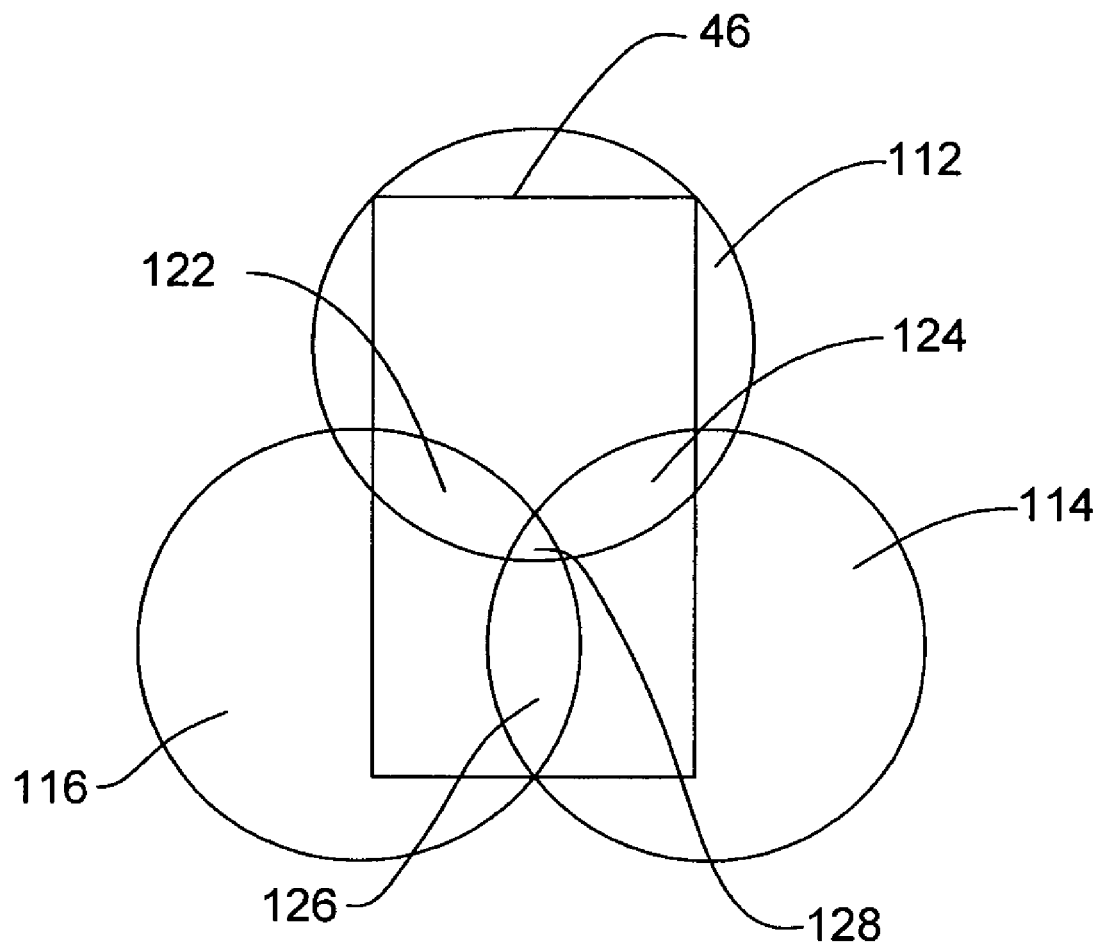
FIG. 16 shows the images projected from the proximal end of the endoscope onto an image sensor.

FIGS. 15 and 16 show an additional embodiment of the endoscope 50. FIG. 15 shows side lenses 102, 104, 106 spaced on the distal tip end 48 of the endoscope. No central lens is present in this embodiment. Illuminating fibers 58 (only some of which are shown) are provided on the surface at the distal tip end 48 of the endoscope, except for the lenses 102, 104, 106. The plurality of fiber optics 58 are connected to a light source 20 and project light outwardly from the distal end 48 of the endoscope. The light provides illumination so that the endoscope 50 may view an anatomical structure in the interior of a patient's body.

As in the earlier embodiments, reflected light images pass through the lenses 102, 104, 106 at the distal tip end 48 of the endoscope and into imaging channels (not shown). The images pass through the imaging channels and are refocused by a lens coupler to form corresponding images 112, 114, 116 as shown in FIG. 16. The projected images 112, 114, 116 overlap respective adjacent images in cross-over areas 122, 124, 126. Further, at overlapping region 128, the three images completely overlap each other. The images 112, 114, 116 cover the entirety of the image sensor 46. In this embodiment, the images 112, 114, 116 and the endoscope 50 are fixed relative to the image sensor 46.

In one embodiment, optical blocking elements 90 block portions of the images 112, 114, 116 at overlapping crossover areas 122, 124, 126, 128 so that the image sensor 46 shown in FIG. 16 receives a single image thereon without overlapping images.

In another embodiment, the image processing device 49 can include image correction algorithms or software filters instead of blocking elements 90 to eliminate the effect of the multiple images applied in the cross-over areas 122, 124, 126, and the triple cross-over area 128.

Figure 17:
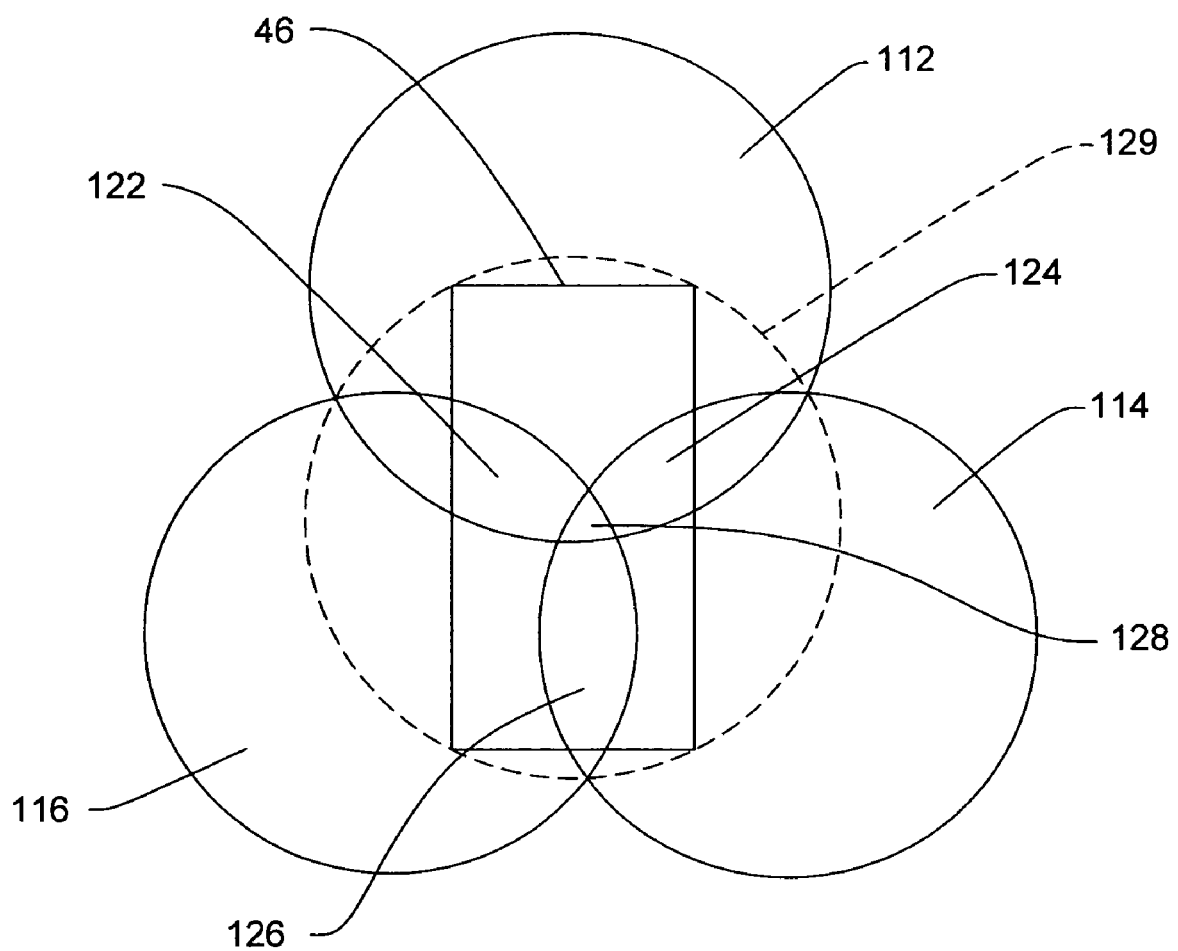
FIG. 17 shows the rotatable images from the proximal end of the endoscope projected onto an image sensor.

In another embodiment shown in FIG. 17, the endoscope 50 is rotatable relative to the image sensor 46 of the camera 14. Rotation of the endoscope 50, and thus the corresponding images 112, 114, 116, allows the orientation of the images to change. The images 112, 114, 116 cover the entirety of the image sensor 46 within the dashed circle line 129 no matter what the angle of rotation is. This embodiment allows the orientation of the processed image viewed on a display screen to remain viewable during the entire rotation of the endoscope 50. As in the earlier described embodiments, blocking elements or image correction algorithms eliminate the effect of the overlapping images in cross-over areas 122, 124, 126, 128.

While the embodiments of FIGS. 15-17 show three essentially circular shaped images 112, 114, 116 that overlap with each other, other embodiments including more than three lenses that provide more than three overlapping images are contemplated. For example, another embodiment has four lenses (not shown) that are preferably symmetrically located about a distal tip end 48 of an endoscope. The four lenses provide four images 130, 132, 134, 136 as shown in FIG. 18 that project from the proximal end of the endoscope onto an image sensor 46.

Figure 18:
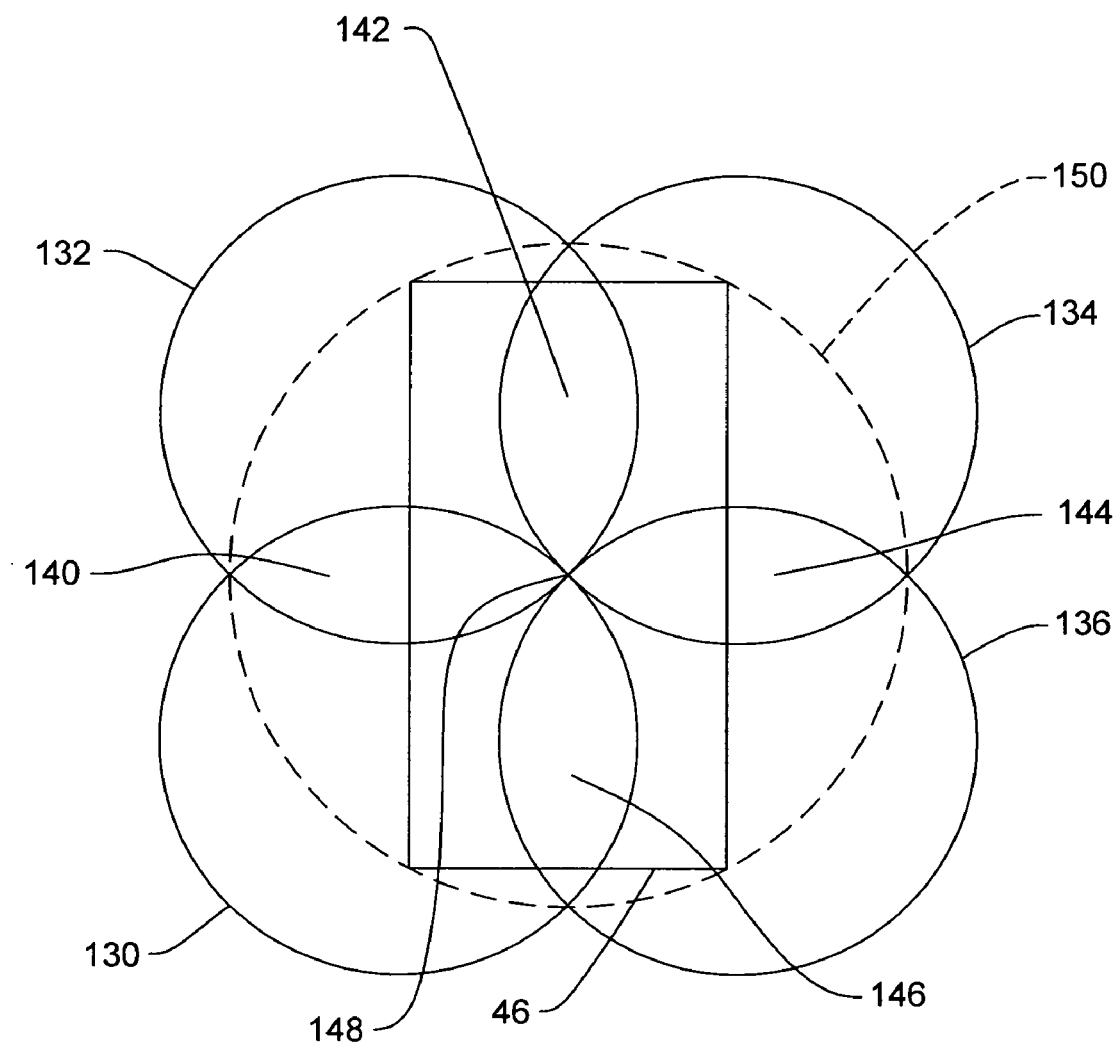
FIG. 18 shows another embodiment having four images from the proximal end of the endoscope projected onto an image sensor.

In FIG. 18, the projected images 130, 132, 134, 136 overlap adjacent images at cross-over areas 140, 142, 144, 146. At a central point 148, the images 130, 132, 134, 136 all meet each other, but are not intended to overlap with each other in most embodiments. The dashed circle line 150 in FIG. 18 shows the innermost position of the outer edges of the images 130, 132, 134, 136 with respect to the image sensor 46 during rotation of the endoscope. Thus the images 130, 132, 134, 136 continue to cover the entirety of the image sensor 46 during rotation of the endoscope.

Figure 10:
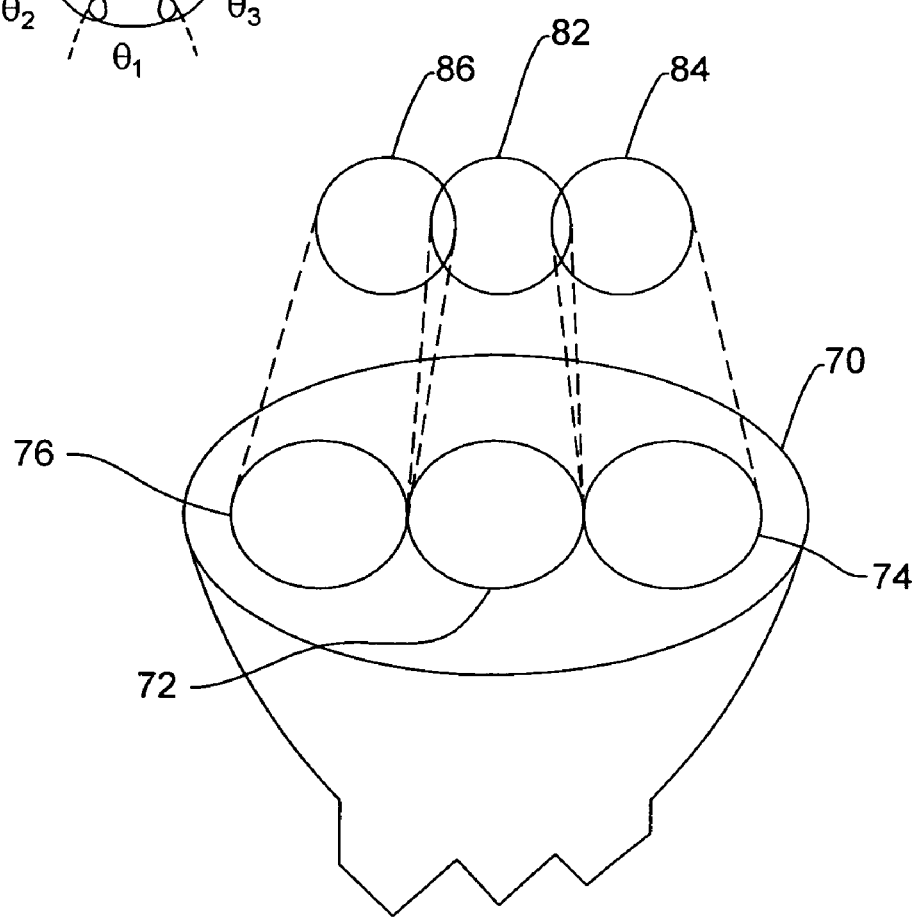
FIG. 10 shows an enlarged perspective view of the proximal end of the endoscope of FIG. 5 and the areas of images projecting therefrom.

While an optical coupler 51 is disclosed, in some embodiments individual refocusing lenses or blockers are provided at the apertures 72, 74, 76 shown in the FIG. 10 embodiment as a substitute for the coupler. Other embodiments of the invention may also use this arrangement.

While various arrangements with different corresponding lenses for the endoscope 50 are shown in the above embodiments, in an additional embodiment a pair of imaging lenses with a pair of corresponding imaging channels extending through the endoscope provide two images that cover the entire surface of an imaging sensor 46. The imaging lenses preferably are equidistant from the longitudinal axis 57 of the endoscope. An overlapping area or cross-over region of the two images can be blocked, removed or accounted for by an optic coupler 51 having a blocking element or by an algorithm or software filter in an image processing device 49 as discussed above with respect to other embodiments.

The endoscope 50 can have a plurality of channels. The endoscope 50 preferably includes from two to five imaging channels, and most preferably three imaging channels 62, 64, 66 as discussed above.

While the imaging channels are shown as circular cylindrical shaped channels, the channels may be rounded and provided with elliptical shapes or other shapes. As discussed above, however, a square or rectangular shape for the image channels is generally undesirable.

In some embodiments the lenses 52, 54, 56 and the corresponding image channels 62, 64, 66 have the same size. In other embodiments, selected lenses and corresponding image channels have different dimensions relative to each other. Thus the projected images have different sizes.

While FIG. 5 shows an external light source 20 providing light to fiber optics 58, in some embodiments LEDs within the endoscope 50 provide illuminating light to the distal end 48 through fiber optics 58. In other embodiments each LED provides light to a plurality of fiber optics 58 or the like. Further, in some embodiments LEDs are provided at the distal tip end 48 of the endoscope.

In another embodiment, a transmitter 99 shown in broken line in FIG. 5 and located within the camera, sends a wireless signal of the sensed images. In one embodiment, the wireless signals are RF signals. In other embodiments, wireless signals are ultra-wide band (WWB), WiFi signals or the like. A receiver 100 illustrated in broken line within the image processing device 49 in FIG. 5 receives the wireless signals. Thus, in this embodiment the cable 18 is not required.

The above described embodiments provide a high definition panoramic image for a display generally having an aspect ratio of 16:9.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. An elongate wide viewing angle endoscope having a proximal end and a distal end comprising:
   at least two rounded optical imaging channels at a distal end of said endoscope;
   an image sensor arrangement for sensing rounded images that overlap and are provided by the rounded optical imaging channels; and
   an image processing device for receiving an output from the image sensor arrangement.

2. The endoscope of claim 1, including at least two concave lenses having an elliptical or circular shape and disposed at the distal end of the endoscope, each said concave lens being in alignment with a corresponding said optical imaging channel, wherein the imaging channels comprise rod lens systems that are aligned parallel to each other.

3. The endoscope of claim 1, including at least two concave lenses having an elliptical or circular shape and disposed at the distal end of the endoscope, each said concave lens being in alignment with a corresponding said optical imaging channel, wherein the imaging channels comprise fiber optic systems that are aligned parallel to each other.

4. The endoscope of claim 1, wherein each said rounded imaging channel has a different angle of view at a distal end with respect to a longitudinal axis of the endoscope, and wherein said image sensor arrangement is provided with a rectangular shape for receiving the rounded images from the rounded optical imaging channels.

5. An elongate wide viewing angle endoscope having a proximal end and a distal end comprising:
   at least two rounded optical imaging channels at a distal end of said endoscope, said imaging channels having fields of view that define at least one cross-over area whereat a rounded image from a first one of said imaging channels overlaps a rounded image from a second one of said imaging channels;
   an image sensor arrangement for sensing the rounded images that include the at least one cross-over area provided by the rounded optical imaging channels; and
   an image processing device for receiving an output from the image sensor arrangement.

6. The endoscope of claim 5, including at least a third said rounded optical imaging channel, wherein said image sensor arrangement is provided with a rectangular shape, and wherein said image processing device obtains a third said rounded image from said third imaging channel that overlaps the first and second images at a portion of the cross-over area so that three overlapping images are provided thereat, the processing device removing two of the three images at the portion of the cross-over area.

7. The endoscope of claim 5, further including an optic coupler having at least one of secondary optics, mechanical stoppers, mechanical blockers, and optical image stoppers for eliminating the image of at least one of said imaging channels at the at least one cross-over area to provide a view utilizing only one image at the cross-over area to the image sensor arrangement.

8. An elongate wide viewing angle endoscope having a proximal end and a distal end comprising:
   at least two rounded optical imaging channels at a distal end of said endoscope, each said imaging channel having a circular or elliptical shape along a length thereof;
   an image sensor arrangement for sensing rounded images provided by the rounded optical imaging channels, said image sensor arrangement having a rectangular shape for receiving the rounded images from the imaging channels; and
   an image processing device for receiving an output from the image sensor arrangement and eliminating all portions of the rounded images that overlap except one said image from one of said channels for displaying a single display image formed by the images from the imaging channels.

9. The endoscope of claim 1, wherein said optical imaging channels extend from the distal end to the proximal end of the endoscope.

10. The endoscope of claim 9, wherein said image sensor arrangement comprises a camera located at the proximal end of said endoscope for receiving the images from said optical imaging channels.

11. The endoscope of claim 8, including a light source located within the endoscope, and including at least two concave lenses having an elliptical or circular shape and disposed at the distal end of the endoscope, each said concave lens being in alignment with a corresponding said optical imaging channel, and wherein said image sensor arrangement comprises a single sensor having a rectangular shape.

12. The endoscope of claim 1, wherein said image processing device includes means for receiving electrical signals from imaging sensors of said image sensor arrangement, said imaging sensors comprising at least one of CCD, CMOS or other imaging elements.

13. The endoscope of claim 1, wherein the distal tip end of said endoscope has a flat surface oriented transverse to a longitudinal axis of the endoscope to provide a cylindrical shape.

14. The endoscope of claim 1, wherein the image sensor arrangement is located at or adjacent the distal end of the endoscope.

15. The endoscope of claim 13, wherein the imaging channels extend essentially parallel with a longitudinal axis of the endoscope from the distal end to the proximal end of the endoscope.

16. The endoscope of claim 1, wherein the image sensor arrangement has a rectangular shape with a 16:9 aspect ratio for receiving the rounded images from the imaging channels, the endoscope including a display for receiving a high definition rectangular image having an aspect ratio of 16:9 from the image processing device.

17. The endoscope of claim 1, wherein the imaging channels comprise at least three said imaging channels aligned parallel to each other, the imaging channels opening in a row across the distal tip end so that a combined field of view for the rounded images from the imaging channels form overlapping concentric patterns.

18. The endoscope of claim 1, wherein the images sensed by said image sensor arrangement from at least two said rounded optical imaging channels are combined by said image processing device to provide a field of view angle that is wider than the field of view angle from any one said image sensed by any one of the imaging channels.

19. The endoscope of claim 5, wherein the image processing device includes image correction algorithms or software filters for eliminating all portions of the rounded images at the cross-over area except one said image from one of said imaging channels to display a single display image formed by the images from the imaging channels.

20. An elongate wide viewing angle endoscope having a proximal end and a distal end comprising:
   at least two and no more than five rounded optical imaging channels at a distal end of said endoscope;
   an image sensor arrangement for sensing rounded overlapping images provided by the rounded optical imaging channels, the rounded overlapping images completely enclosing the image sensor arrangement and defining at least one cross-over area; and
   an image processing device for receiving an output from the image sensor arrangement.

21. The endoscope of claim 1, including a transmitter for receiving the rounded images from the image sensor arrangement and wirelessly transmitting the rounded images, and a receiver for receiving the wirelessly transmitted rounded images from the transmitter and providing the rounded images to the image processing device.

22. The endoscope of claim 20, wherein the endoscope is rotatable relative to the image sensor arrangement, and wherein the image processing device processes the output of the image sensor arrangement with an algorithm or software filter to eliminate overlap of the images at the at least one cross-over area.

* * * * *